United States Patent [19]

Heinemann et al.

[11] 4,434,292
[45] Feb. 28, 1984

[54] PROCESS FOR THE PREPARATION OF PYRAZOLE

[75] Inventors: Ulrich Heinemann; Rudolf Thomas, both of Wuppertal; Reinhard Lantzsch, Leverkusen; Klaus Ditgens; Erhard Weber, both of Wuppertal, all of Fed. Rep. of Germany

[73] Assignee: Bayer Aktiengesellschaft, Leverkusen, Fed. Rep. of Germany

[21] Appl. No.: 300,329

[22] Filed: Sep. 8, 1981

[30] Foreign Application Priority Data

Sep. 19, 1980 [DE] Fed. Rep. of Germany ....... 3035395

[51] Int. Cl.³ .......................................... C07D 231/12
[52] U.S. Cl. ..................................... 548/373; 548/379
[58] Field of Search .......................................... 548/373

[56] References Cited

U.S. PATENT DOCUMENTS 2,515,160 7/1950 Copenhaver ........................ 548/373

FOREIGN PATENT DOCUMENTS 1234223 2/1967 Fed. Rep. of Germany .
2648008 5/1978 Fed. Rep. of Germany .
2704281 8/1978 Fed. Rep. of Germany .

OTHER PUBLICATIONS

Wirsing, Journal für Praktische Chemie, 1894, vol. 50, pp. 531–554.
Wolfe et al., Chem. Abst., 1971, vol. 74, No. 35102q.
MacLean, Chem. Abst., 1969, vol. 70, No. 28391x.

Primary Examiner—John M. Ford
Assistant Examiner—Bernard Dentz
Attorney, Agent, or Firm—Felfe & Lynch

[57] ABSTRACT

Process for the preparation of pyrazole from hydrazine hydrate and acrolein comprising reacting hydrazine hydrate with acrolein in an aqueous-organic medium at a temperature between 20°–80° C. and then oxidizing the 2-pyrazoline formed, of the formula

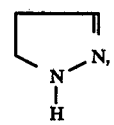

(I)

either directly or after first being isolated, with chlorine or an alkali metal hypochlorite or an alkaline earth metal hypochlorite and water or an aqueous-organic medium at a temperature between 0° and 60° C.

5 Claims, No Drawings

PROCESS FOR THE PREPARATION OF PYRAZOLE

This invention relates to a process for the preparation of pyrazole. This compound is useful as a starting substance for the synthesis of herbicidally active acetanilides.

It is known that pyrazole is obtained when hydrazine hydrate and acrolein are first reacted in the presence of ether, as a diluent, and with cooling, to give 2-pyrazoline, this compound is isolated in the form of its hydrochloride, the base is then liberated in the customary manner and the 2-pyrazoline is subsequently oxidized with bromine in the presence of chloroform, as a diluent, to give pyrazole (see Journal f.Praktische Chemie 50, 531 et seq. (1894)). However, this process has a number of disadvantages. Thus, the preparation of 2-pyrazoline must be carried out with cooling. Furthermore, the 2-pyrazoline can evidently be isolated from the reaction mixture only in the form of its hydrochloride, which must additionally also be purified by an exceptionally expensive process. 2-Pyrazoline hydrochloride is obtained thereby in yields of about 50% of theory, and the yield is further reduced during conversion of the salt into the free base, which is subsequently necessary, and further purification of the base by extraction and distillation.

The oxidation in the subsequent second stage also proceeds in an unsatisfactory manner, since the yield is only about 40%. Furthermore, bromine is not an ideal oxidising agent, especially for use on an industrial scale.

The present invention now provides a process for the preparation of pyrazole from hydrazine hydrate and acrolein, characterized in that hydrazine hydrate is reacted with acrolein in an aqueous-organic medium at a temperature between 20° and 80° C. and the 2-pyrazoline formed, of the formula

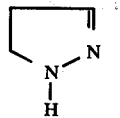

(I)

is oxidized either directly, or where appropriate after first being isolated, with chlorine or an alkali metal hypochlorite or an alkaline earth metal hypochlorite in water or an aqueous-organic medium at a temperature between 0° and 60° C., if necessary in the presence of a catalyst.

It is to be described as exceptionally surprising that the process according to the invention proceeds with good yields under the reaction conditions mentioned, since, on the basis of the fact that acrolein partially polymerises, even with cooling, in the case of the known process (in this context, see the abovementioned literature reference), it had to be expected that increased polymerisation would occur if the reaction were carried out without cooling.

It is also surprising that it is possible to isolate the pyrazoline smoothly from the reaction mixture, since the difficulty of isolating pyrazoline from aqueous solutions is generally known (in this context, see also the abovementioned literature reference).

The smooth oxidation of pyrazoline to give pyrazole is also surprising inasmuch as exclusively the desired unsubstituted pyrazole is formed. Since chlorine tends to substitute the nucleus more so than does bromine, the formation of chlorinated pyrazoles, in particular 4-chloro-pyrazole, was to be expected (in this context, see also Liebigs Ann. der Chemie 598, 186 (1956)).

The process according to the invention is distinguished by a number of advantages. Thus, with the aid of this process, it is possible to prepare pyrazole in high yields in a simply manner, even on an industrial scale. It should be particularly emphasised that virtually no by-products are formed and that the working up presents no difficulties at all. In addition, the pyrazoline of the formula (I) obtained as the intermediate product can be isolated in a simple manner if desired. The process according to the invention thus represents a valuable enrichment of the art.

The course of the process according to the invention can be illustrated by the following equation:

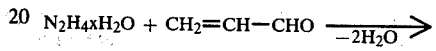

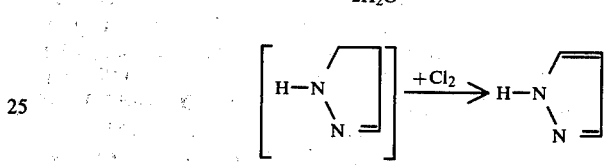

Preferred organic solvent components of the aqueous-organic medium used in the process according to the invention are aromatic hydrocarbons (such as benzene, toluene and xylene), or aromatic halogenated hydrocarbons (such as chlorobenzene or dichlorobenzene).

In principle, other customary organic solvent can also be used, such as chloroform.

The reaction temperatures can be selected within the mentioned substantial range in carrying out the process according to the invention. The reaction of hydrazine hydrate and acrolein is carried out at a temperature between 20° and 80° C., preferably at a temperature between 20° and 60° C. The subsequent oxidation of pyrazoline of the formula (I) to give pyrazole is carried out at a temperature between 0° C. and 60° C., preferably at a temperature between 0° C. and 30° C.

If necessary, the oxidation of 2-pyrazoline to give pyrazole can be carried out in the presence of a catalyst. The customary oxidation catalysts are used for this, such as ruthenium dioxide monohydrate or ruthenium trichloride monohydrate.

In carrying out the process according to the invention, 1 to 1.2 moles of acrolein are preferably employed per mole of hydrazine hydrate, and 1 to 2 moles of chlorine or alkali metal hypochlorite or alkaline earth metal hypochlorite (such as, preferably, sodium hypochlorite, potassium hypochlorite or calcium hypochlorite) are employed per mole of 2-pyrazoline formed.

The process according to the invention is in general carried out under atmospheric pressure. However, it is also possible to carry out the process under increased or reduced pressures.

If desired, the 2-pyrazoline formed as the intermediate product can be isolated by heating the reaction mixture under reflux, using a water separator in order thus to remove the water from the system. The residue is concentrated in vacuo. The resulting crude 2-pyrazoline can be purified by further distillation in vacuo over a column.

The pyrazoline can be further reacted in the pure form, in the form of its organic solution, after removing the water from the system, or directly in the aqueous-organic solution.

In detail, the process according to the invention is carried out by a procedure in which acrolein is added to hydrazine hydrate in an organic solvent and, after the subsiding of the highly exothermic reaction, either the water is first removed from the reaction mixture (in order then to isolate the pyrazoline), or the oxidising agent is added directly to the reaction mixture, with cooling. Subsequent working up is carried out by customary methods. In general, a procedure is followed in which, when the oxidation has ended, the reaction mixture is stirred with an aqueous alkali metal base and then extracted several times with an organic solvent of low miscibility with water, and the combined organic phases are dried and concentrated. Pyrazole is thereby obtained in a pure form.

The pyrazole which can be prepared by the process according to the invention is a generally interesting synthesis unit in organic chemistry. In particular, pyrazole can be used as a starting substance for the synthesis of herbicidally active acetanilides (see DE-OS (German Published Specification) No. 2,648,008 and DE-OS (German Published Specification) No. 2,704,281).

Thus, for example, 2,6-diethyl-N-(pyrazol-1-yl-methyl)-chloroacetanilide can be prepared by reacting 2,6-diethyl-N-chloromethyl-chloroacetanilide with pyrazole in the presence of a diluent and in the presence of an acid-binding agent. This synthesis can be represented by the following equation:

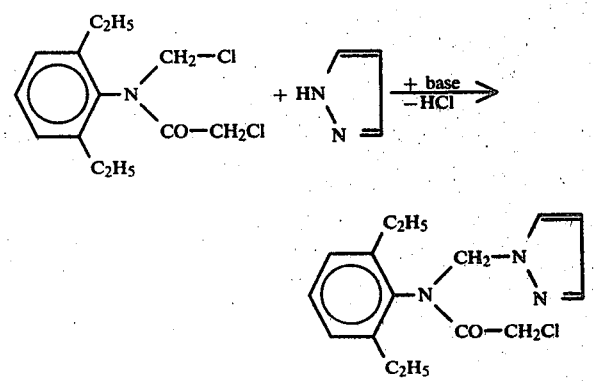

The process according to the invention is illustrated by the following examples.

Preparative Examples

Example 1 (with isolation of 2-pyrazoline)

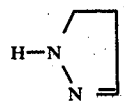

(a) 268.8 g (4.8 moles) of acrolein were added to 200 g (4 moles) of hydrazine hydrate in 600 ml of toluene, whilst stirring. After the subsiding of the highly exothermic reaction (about 60° C.), the reaction mixture was heated under reflux, using a water separator, until the calculated amount of water (144 ml) had been separated off. The solution which remained was concentrated by distilling off the toluene in vacuo over a column. 227 g (81% of theory) of 2-pyrazoline were obtained as a colourless oil of boiling point 50° C./24 mbar.

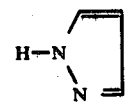

(b) 24.7 g (0.35 mole) of chlorine were passed into 24.4 g (0.35 mole) of the resulting 2-pyrazoline in 500 ml of toluene, whilst cooling with ice and stirring vigorously. The reaction mixture was stirred for 30 minutes and concentrated, and 280 ml of 20% strength aqueous sodium hydroxide solution were added to the residue. The mixture was stirred again for 30 minutes and then extracted five times with 500 ml of ether each time. The combined organic phases were dried over sodium sulphate and concentrated. 17 g (72% of theory) of pyrazole of melting point 69° to 70° C. were obtained.

(c) 12 g (0.17 mole) of chlorine were passed into 7 g (0.1 mole) of the 2-pyrazoline, obtained according to (a), in 22 ml of water at 10° to 25° C. (ice-cooling) whilst stirring vigorously. The mixture was subsequently stirred at room temperature for 30 minutes, and 16 g (0.4 mole) of sodium hydroxide in 44 ml of water were added. The mixture was then extracted four times with 75 ml of methylene chloride each time. The combined organic phases were dried over sodium sulphate and concentrated in vacuo. The oil which remained rapidly crystallised completely. 4.9 g (72% of theory) of pyrazole of melting point 68°-69° C. were obtained.

Example 2 (without isolation of 2-pyrazoline)

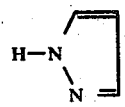

140 g (2 moles) of chlorine were passed into a reaction solution, obtained according to Example 1 (process step (a)), of 70 g (1 mole) of 2 pyrazoline (determined by gas chromatography) in toluene/water at 10°-25° C. (ice-cooling) whilst stirring vigorously. The mixture was subsequently stirred at room temperature for 30 minutes and was concentrated in vacuo. After adding 800 g of 20% strength aqueous sodium hydroxide solution, the mixture was subsequently stirred for a further 30 minutes. It was then extracted four times with 1,000 ml of methylene chloride each time, and the combined organic phases were dried over sodium sulphate and concentrated. The oily residue rapidly crystallised completely. 56 g (83% of theory) of pyrazole of melting point 69° C. were obtained.

Examples of the use of pyrazole for the synthesis of a herbicidally active acetanilide Example I

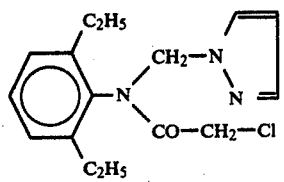

A mixture of 68 g (1 mole) of pyrazole and 106 g (1.05 moles) of triethylamine in 150 ml of anhydrous ethyl acetate were added to 274.2 g (1 mole) of 2,6-diethyl-N-chloromethyl-chloroacetanilide in 250 ml of anhydrous ethyl acetate, whilst stirring; during this addition, the temperature rose to 30° C. The mixture was subsequently stirred at room temperature for 1 hour. There were two possible methods of working up:

(a) The reaction mixture was filtered and the filtrate was washed with water until neutral, dried over sodium sulphate and evaporated in vacuo. After fractional crystallisation of the residue with ligroin, 171.2 g (56% of theory) of 2,6-diethyl-N-(pyrazol-1-yl-methyl)-chloroacetanilide of melting point 67° were obtained in the form of colourless crystals.

(b) The reaction mixture was cooled to 0° C. and filtered and the residue on the filter was rinsed with 10 ml of cold ethyl acetate. 50 g (1.4 moles) of dry hydrogen chloride were passed into the filtrate at 0° to −10° C. The hydrochloride salts which had precipitated were then filtered off and rinsed with 50 ml of cold ethyl acetate, and the solid residue was partitioned between 0.5 liter of ethyl acetate and 0.5 liter of aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colourless oily residue, whereupon the residue crystallised. 220.2 g (72% of theory) of 2,6-diethyl-N-(pyrazol-1-yl-methyl)-chloroacetanilide of melting point 67° C. were obtained in the form of colourless crystals.

It will be understood that the specification and examples are illustrative but not limitative of the present invention and that other embodiments within the spirit and scope of the invention will suggest themselves to those skilled in the art.

What is claimed is:

1. Process for the preparation of pyrazole from hydrazine hydrate and acrolein comprising reacting hydrazine hydrate with acrolein in an organic medium at a temperature between 20°–60° C. and then oxidizing the 2-pyrazoline formed, of the formula

 (I)

either directly or after first being isolated, with chlorine or an alkali metal hypochlorite in the presence of water or an aqueous-organic medium at a temperature between 0° and 30° C.

2. Process as claimed in claim 1 wherein an aromatic hydrocarbon or an aromatic halogenated hydrocarbon is used as the organic solvent component of the aqueous-organic medium.

3. Process as claimed in claim 1 wherein sodium hypochlorite or potassium hypochlorite is used as the oxidizing agent.

4. Process as claimed in claim 1 wherein chorine is used as the oxidizing agent.

5. Process as claimed in claim 1 wherein acrolein is added to hydrazine hydrate in a mole ratio of about 1.2:1 in toluene, the reaction mixture is heated under reflux and the remaining solution is concentrated by distilling off the toluene over a column to yield 2-pyrazoline, about 0.1 mole of chlorine is passed into the resulting 2-pyrazoline in toluene while cooling with ice and stirring, the reaction mixture is stirred and concentrated, aqueous sodium hydroxide is added to the residue, the mixture is again stirred and extracted with ether, and the combined organic phases are dried over sodium sulphate and concentrated to yield pyrazole.

* * * * *